United States Patent
DiMarzio et al.

(10) Patent No.: US 7,462,809 B2
(45) Date of Patent: Dec. 9, 2008

(54) SPECTRAL FILTER SYSTEM FOR INFRARED IMAGING OF SUBSTRATES THROUGH COATINGS

(75) Inventors: Donald DiMarzio, Northport, NY (US); John Douglas Weir, Huntington, NY (US); Steven Chu, Ronkonkoma, NY (US); Nils Jakob Fonneland, Lake Grove, NY (US); Dennis John Leyble, Great River, NY (US)

(73) Assignee: Northrop Grumman Corporation, Los Angeles, CA (US)

( * ) Notice: Subject to any disclaimer, the term of this patent is extended or adjusted under 35 U.S.C. 154(b) by 0 days.

(21) Appl. No.: 11/506,701

(22) Filed: Aug. 18, 2006

(65) Prior Publication Data

US 2006/0289766 A1   Dec. 28, 2006

Related U.S. Application Data

(63) Continuation-in-part of application No. 10/971,217, filed on Oct. 22, 2004, now Pat. No. 7,164,146.

(51) Int. Cl.
*H01L 27/00* (2006.01)
(52) U.S. Cl. .................... 250/208.1; 250/559.4
(58) Field of Classification Search .............. 250/208.1, 250/559.4, 559.45, 338.1–338.3; 356/239.1–239.2
See application file for complete search history.

(56) References Cited

U.S. PATENT DOCUMENTS

| 3,973,122 A | * | 8/1976 | Goldberg ............... 250/338.1 |
| 4,484,081 A | | 11/1984 | Cornyn, Jr. et al. |
| 4,647,220 A | | 3/1987 | Adams et al. |
| 4,682,222 A | | 7/1987 | Smith et al. |
| 4,783,166 A | * | 11/1988 | Stern ....................... 356/36 |
| 4,878,116 A | | 10/1989 | Thomas et al. |
| 4,988,875 A | | 1/1991 | Ortiz et al. |
| 5,065,630 A | | 11/1991 | Hadcock et al. |
| 5,258,705 A | | 11/1993 | Okamoto et al. |
| 5,287,183 A | | 2/1994 | Thomas et al. |
| 5,703,362 A | | 12/1997 | Devitt et al. |
| 5,763,786 A | | 6/1998 | Camplin et al. |
| 5,782,974 A | | 7/1998 | Sorensen et al. |

(Continued)

FOREIGN PATENT DOCUMENTS

WO    WO 01/20319    3/2001

*Primary Examiner*—Que T Le
(74) *Attorney, Agent, or Firm*—Alan G. Towner, Esq.; Pietragallo Gordon Alfano Bosick & Raspanti, LLP

(57) ABSTRACT

An improved system for visual inspection of substrates coated with paints and polymers is disclosed. Painted substrates can be inspected for environmental and physical damage such as corrosion and cracks without removing the paint. The present invention provides the ability to maximize paint thickness penetration. This is accomplished with a spectral bandpass filter that rejects reflected light from the coating opaque bands, while allowing light in the paint window to pass to an IR detector such as an IR camera focal plane. The narrow bandpass range enhances the ability for IR imaging to see through thicker paint layers and improves the contrast over standard commercial IR mid-wave cameras. The bandpass may be adjusted to coincide with the full spectral window of the paint, consistent with the ability of the imaging focal plane to detect light in the spectral region.

20 Claims, 5 Drawing Sheets

U.S. PATENT DOCUMENTS

| | | | |
|---|---|---|---|
| 5,900,632 A | 5/1999 | Sterling et al. | |
| 5,963,653 A | 10/1999 | McNary et al. | |
| 6,000,844 A | 12/1999 | Cramer et al. | |
| 6,012,840 A | 1/2000 | Small, IV et al. | |
| 6,049,081 A | 4/2000 | Sterling et al. | |
| 6,160,625 A | 12/2000 | Damer et al. | |
| 6,184,528 B1 | 2/2001 | DiMarzio et al. | |
| 6,269,179 B1 | 7/2001 | Vachtsevanos et al. | |
| 6,399,949 B1 | 6/2002 | Roney, Jr. et al. | |
| 6,452,180 B1 | 9/2002 | Nistler et al. | |
| 6,471,396 B2 | 10/2002 | Biel | |
| 6,495,833 B1 | 12/2002 | Alfano et al. | |
| 6,517,236 B2 | 2/2003 | Sun et al. | |
| 6,517,238 B2 | 2/2003 | Sun et al. | |
| 6,853,926 B2 | 2/2005 | Alfano et al. | |
| 6,873,680 B2 | 3/2005 | Jones | |
| 2002/0050566 A1 | 5/2002 | Nilsson et al. | |
| 2004/0026622 A1 | 2/2004 | DiMarzio et al. | |
| 2005/0031974 A1 | 2/2005 | Fukuhara | |
| 2005/0056786 A1 | 3/2005 | Shepard et al. | |
| 2005/0061247 A1 | 3/2005 | Shibata et al. | |

\* cited by examiner

Gloss P1T1 Sample
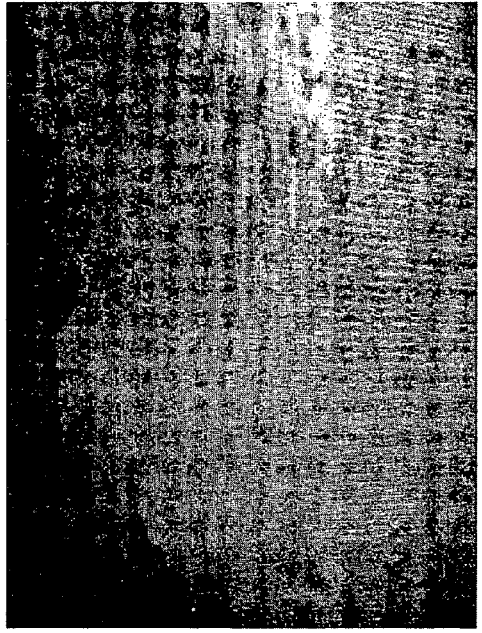
FIG. 6  3.5-5 μm
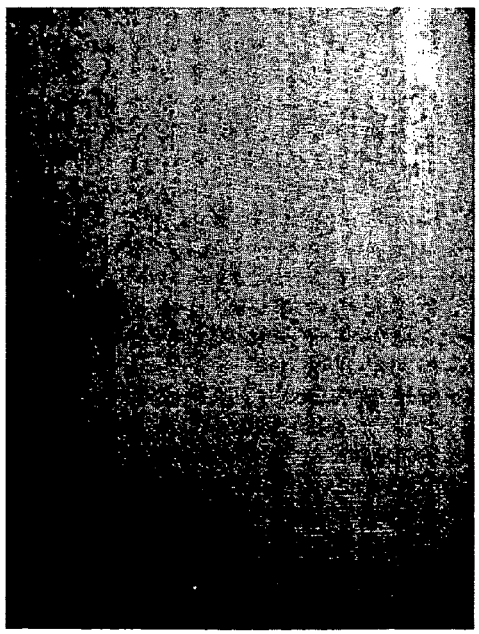
FIG. 5  3-5 μm
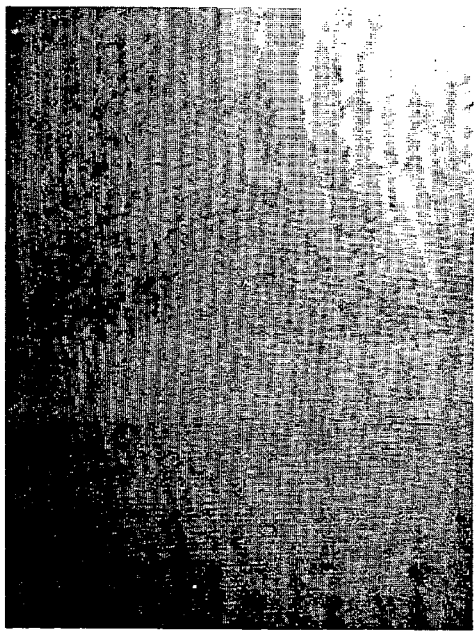
FIG. 7  3.75-5 μm 3.5-5 μm 3-5 μm: STANDARD FILTER 3.75-5 μm: OPTIMIZED FILTER Camo P2T2 Sample

SPECTRAL FILTER SYSTEM FOR INFRARED IMAGING OF SUBSTRATES THROUGH COATINGS

CROSS-REFERENCE TO RELATED APPLICATION

This application is a continuation-in-part of U.S. application Ser. No. 10/971,217 filed Oct. 22, 2004, which is incorporated herein by reference.

GOVERNMENT CONTRACT

The United States Government has certain rights to this invention pursuant to Contract No. FA8601-05-F-0011, Subtask 023, awarded by the United States Air Force.

FIELD OF THE INVENTION

The present invention relates to imaging of substrates through coatings, and more particularly relates to a spectral filter system for infrared imaging of defects and other structural features of coated objects such as aircraft components.

BACKGROUND INFORMATION

Aircraft components are subject to constant degradation such as corrosion and cracking caused by environmental and operational conditions. Although the application of coatings, such as paints, reduces corrosion problems substantially, they typically cannot eliminate them entirely. Furthermore, stress experienced during flight can result in damage which a coating of paint cannot mitigate, such as stress defects and cracking. In order to ensure that aircraft are ready for flight, periodic inspections are necessary.

Inspection of aircraft components traditionally includes visual inspection. When visually inspecting aircraft components, the coating used to protect the components becomes an obstacle because it may hide structural defects or features beneath the coating. It is therefore necessary to strip the component assembly or aircraft in question of its paint before a proper visual inspection can be performed. Afterward, a new coating of paint must be applied. This process results in substantial expense in the form of labor and materials, raises environmental concerns, and requires a great amount of time.

Apart from the inefficiency of visual inspection methods, another problem is that visual inspection is not always effective. While a skillful eye may pick up most human-visible defects with a satisfactory degree of consistency, some defects may be very small or lie under the surface of the component. In many cases these defects will go unnoticed by visual inspection regardless of the skill and experience of the observer.

In addition to visual inspection, active thermography techniques have been proposed for inspection of various components. One such technique utilizes a transient heat source to heat the component, followed by detection of a transient heat signature on the surface of the component to determine the presence of anomalies or defects. However, such techniques require specialized equipment and controls to generate the necessary transient heating, and are inefficient because detection of the transient thermal signature can require a significant amount of time.

U.S. Published Patent Application No. US 2004/0026622 A1, which is incorporated herein by reference, discloses a system for imaging coated substrates which utilizes an infrared (IR) light source. The IR light shines on the object and is reflected to a focal plane array.

U.S. application Ser. No. 10/971,217 discloses a system for detecting structural defects and features of coated substrates using a blackbody self-illumination technique.

The present invention has been developed in view of the foregoing.

SUMMARY OF THE INVENTION

One embodiment of the present invention utilizes the substantially steady-state temperature of a coated object, in conjunction with an optical detection system, to selectively view defects and features of the object below the coating without the necessity of transient heating or IR illumination and reflectance imaging. The optical detector, such as an IR camera, may be tailored for the wavelengths at which the coating material is substantially transparent. At least one narrow bandwidth spectral optical filter is positioned between the substrate and the detector. The filter significantly improves viewing clarity of the defects and features under the coating, and distinguishes them from spurious features on the top surface of the coating. The system enables the inspection of small or large areas in real time, without requiring complex image acquisition, storage and image processing equipment and software.

Another embodiment of the present invention provides a system including the use of IR illumination for imaging the surface of a substrate through a coating on the substrate. An infrared light source is positioned to cast infrared light upon the substrate to create reflected light. A detector such as a focal plane array may be positioned to receive the reflected light and generate an image therefrom. At least one narrow bandwidth spectral optical filter is positioned between the substrate and the detector to pass wavelengths of the reflected light which reveal structural features of the substrate.

An aspect of the present invention is to provide a system for imaging the surface of a substrate through a coating on the substrate. The system comprises a detector positioned to receive infrared radiation from the substrate surface, and at least one narrow bandwidth spectral optical filter between the substrate and the detector to pass infrared wavelengths from 3.75 to 5.0 micrometers to the detector.

Another aspect of the present invention is to provide a method for imaging the surface of a substrate through a coating on the substrate. The method comprises generating infrared light from the substrate, filtering the infrared light with a narrow bandwidth filter which passes wavelengths within a range from 3.75 to 5.0 micrometers, and receiving the filtered infrared light on a detector.

These and other aspects of the present invention will be more apparent from the following description.

BRIEF DESCRIPTION OF THE DRAWINGS

FIGS. 5-7 are photographic images of a coated substrate, illustrating unexpectedly improved detection of substrate damage under the coating with a system including a narrow bandwidth filter of the present invention (FIG. 7) in comparison with systems having broader bandwidth filters (FIGS. 5 and 6).

DETAILED DESCRIPTION

The present invention provides improved visual inspection of substrates that are coated with paints and polymers. Most paints and polymer coatings have a region of significantly reduced electromagnetic radiation absorption and scattering in the mid IR region as compared to the visible spectral region. This effectively opens a window of visibility where certain IR imaging cameras can see through coatings to the underlying substrates. Painted substrates can be inspected for environmental and physical damage such as corrosion and cracks without removing the paint.

The present invention provides the ability to maximize paint thickness penetration. This is accomplished with a spectral bandpass filter that rejects reflected light from the coating opaque bands, while allowing light in the paint window to pass to the IR camera focal plane. The narrow bandpass range results in the enhanced ability for IR imaging to see through thicker paint layers. The bandpass may be adjusted to coincide with the full spectral window of the paint, consistent with the ability for the imaging focal plane to detect light in the spectral region. In one embodiment, a suitable camera uses a cooled InSb focal plane array with a sensitivity to IR light which drops to zero for wavelengths longer than about 5.6 micrometers.

In accordance with the present invention, it has been found that extending the bandpass filter to wavelengths beyond 5.0 micrometers actually has a deleterious effect on the image that is produced by the IR camera. This unwanted effect can be explained by the significant increase in thermal radiative flux going to the focal plane in the spectral regions above 5.0 micrometers. For objects at or near room temperature, the natural thermal emission of radiation increases in the mid IR region as the wavelength increases. This means that regions of an object that have low reflectance (high emissivity) and look dark in the IR reflectance image, now start to look lighter since the regions are emitting more of their own radiation in the range above 5.0 micrometers. This results in reduced contrast between the low reflectance regions (e.g., corrosion on metal) and the higher reflectance regions (uncorroded). This reduced contrast makes it more difficult to visually detect regions of corrosion on metals covered with relatively thick paint.

As used herein, the term "narrow bandwidth filter" means that the spectral range for the bandpass filter for IR imaging lies between 3.7 and 5.0 micrometers, for example, between 3.75 and 5.0 micrometers. This applies to the use of active IR illumination of a coated substrate to create the image, or the use of the natural thermal emission of the coated substrate for self-illumination.

Figure 1:
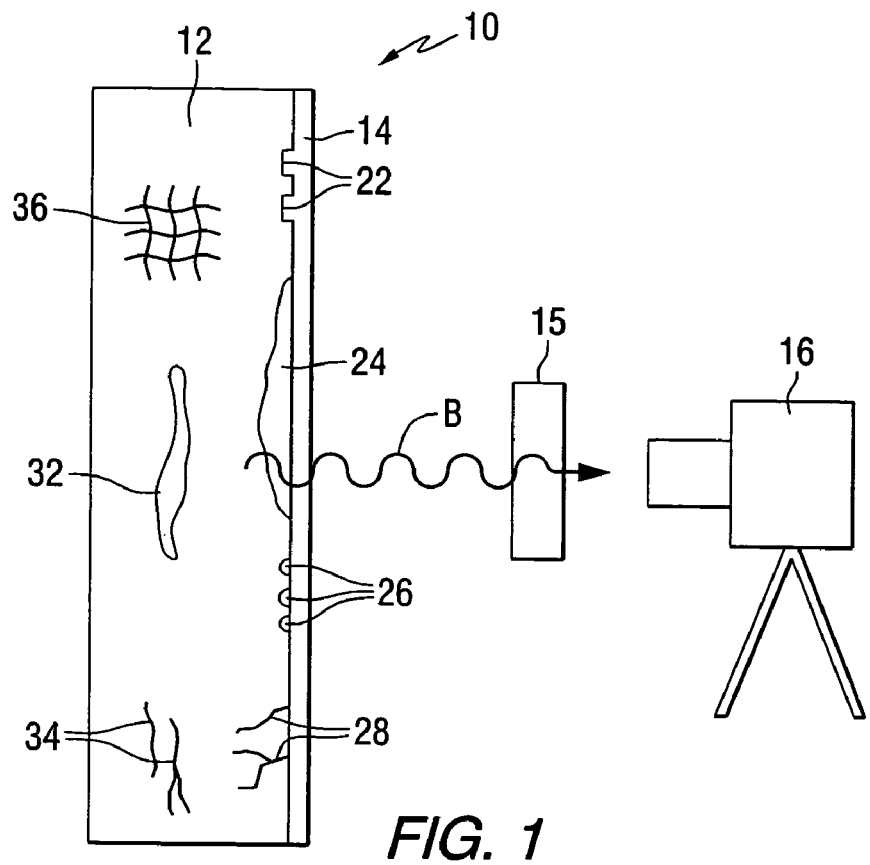
FIG. 1 is a schematic illustration of a system for detecting structural features of a coated object utilizing blackbody self-illumination of the object and a narrow bandwidth filter positioned between the object and a detector.

FIG. 1 schematically illustrates a detection system in accordance with an embodiment of the present invention. A coated object 10, such as an aircraft component, composite panel, painted panel, ship hull, ground vehicle, aircraft assembly, aircraft landing gear, metallic substrate, honeycomb bonded assembly or the like, includes a substrate or object 12 at least partially covered with a coating 14 such as paint, composite matrix material or the like.

Examples of some specific coatings include coatings manufactured to the following specifications: BMS 10-172; BMS 10-11; BMS-10-79, BMS 10-60; MIL-PRF-23377; MIL-PRF-85582; MIL-PRF-85285 and TT-P-2760. In accordance with the present invention, the coatings may be relatively thick while still allowing clear imaging of substrate defects below the coating. For example, the coating 14 may be approximately 0.5 to 12 mils thick.

The object 12 emits blackbody radiation B toward a detector 16 such as an infrared (IR) camera, IR detector or the like. A narrow bandwidth filter 15 is located between the coated object 10 and the detector 16. The narrow bandwidth filter 15 can be single or multiple component filter to obtain the desired bandpass.

In accordance with an embodiment of the present invention, the blackbody radiation B from the object 12 is generated in a substantially steady state. As used herein, the term "substantially steady state blackbody radiation" means the radiation naturally generated from the object to be inspected due to its maintenance at a temperature above zero degrees Kelvin, typically at room temperature or a slightly elevated temperature. Steady state blackbody radiation results from maintaining the object or a portion thereof at a substantially uniform temperature, i.e., in the absence of significant thermal gradients throughout the object or portion thereof being inspected.

Since the object 12 is at or near room temperature, it emits a significant amount of substantially steady state infrared (IR) blackbody thermal radiation B. In contrast, the coating 14 may be substantially transparent at some of the wavelengths at which the underlying object emits the blackbody radiation B. Many organic polymers that may be used in the coating 14 are significantly IR-transmissive in certain spectral bands. The blackbody radiation B of the object can penetrate the organic coating 14 covering the object 12 and reveal the surface condition of the object 12 under the coating 14. The radiation B transmitted through the coating 14 is thus used to provide images from the self-illuminated object 12 that reveal any defects such as corrosion, cracks and pits, as well as other structural features under the coating 14. The object 12 to be inspected becomes observable by its own IR radiation B, which is a function of the temperature of the object 12.

As shown in FIG. 1, the object 12 to be inspected may include various types of structural features. The structural features may be located on the surface of the object 12 under the coating 14, or may be located below the surface of the object 12. For example, surface features 22 may be provided on the surface of the object 12 below the coating 14. Examples of surface features 22 include indicia such as alphanumeric symbols, marks, codes, part numbers, bar codes and the like. The object 12 may also include surface defects such as corrosion 24, pits 26, cracks 28, gouges, and other structural defects. As shown in FIG. 1, the object 12 may also include structural features below the surface of the object 12, such as corrosion 32, cracks 34, composite reinforcements 36 and pits 26.

Figure 2:
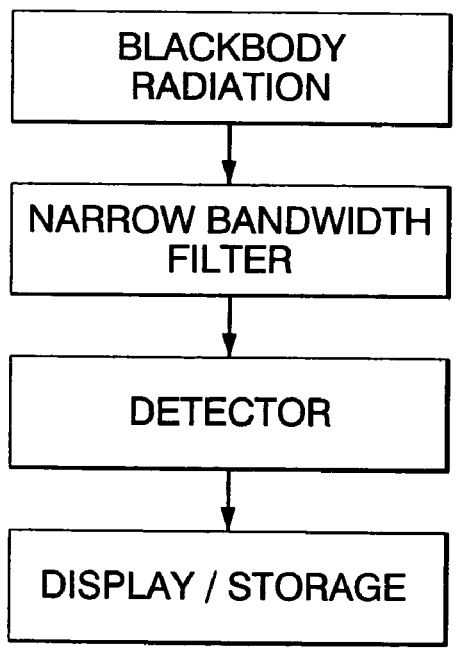
FIG. 2 is a schematic flow diagram illustrating the filtering and detection of blackbody radiation from an object to be inspected in accordance with an embodiment of the present invention.

FIG. 2 schematically illustrates a blackbody radiation detection process in accordance with an embodiment of the present invention. Blackbody radiation from an object such as the coated object 10 shown in FIG. 1 is transmitted through a narrow bandwidth filter to a detector such as an IR camera. After detection, an image of the coated object 12, including structural features of the object 10 under the coating 14 may be displayed and/or stored. In addition, the image may be transmitted by any suitable means such as the Internet, wireless, cable or satellite for display and/or storage at any desired location.

In accordance with an embodiment of the present invention, the steady state blackbody radiation B from the object to be inspected may be generated by holding the object at room temperature. The entire object may be maintained at a substantially uniform temperature at or near room temperature. As used herein, the term "room temperature" means the surrounding ambient temperature found in an area such as a testing laboratory, production facility, warehouse, hanger, airstrip, aircraft cabin or ambient exterior temperature. Room temperatures are typically within a range of from about 60 to about 80° F. However, temperatures above or below such a range may exist. For example, in cold environments such as unheated hangers or warehouses in cold regions, the room temperature may be 32° F. or lower. In warm environments such as non-air-conditioned hangers and warehouses in desert or tropical regions, the "room temperature" may be well above 80° F., e.g., up to 100 or 110° F., or even higher.

In accordance with another embodiment of the present invention, the object to be inspected is held at an elevated temperature, e.g., above room temperature, to maintain the substantially steady state blackbody radiation. Such an elevated temperature may be up to about 120° F. or higher, typically in a range of from 80 to about 110° F. The elevated temperature may be maintained by any suitable means, such as exposure to sunlight, heat gun, heat lamp, thermal blanket, hot packs, human contact and the like.

The detector 16 may selectively detect radiation at certain wavelengths at which the coating 14 is substantially transparent. In this manner, the coating 14 does not substantially interfere with the image from the object 12. The detector 16 may include any suitable device such as an IR camera, IR detector, IR focal plane or the like. For example, the camera may be an analog or digital camera, and may record still or video images. The detector 16 may include a portable or movable camera such as a hand-held camera or a camera that may be mounted on a tripod or the like that can be moved by means of a pan feature and/or a tilt feature. Infrared cameras may be used, for example, cameras which detect mid-infrared radiation, e.g., having wavelengths between about 3 and about 5 microns. Such mid-IR wavelengths have been found to produce relatively sharp images with minimal interference from several types of coatings.

In addition to the camera 16, the narrow bandwidth filter 15 is positioned in the optical path of the blackbody radiation B between the object 12 and the detector 16. The narrow bandwidth filter 15 removes portions of the blackbody radiation B having wavelengths at which the coating 14 is non-transparent, e.g., wavelengths below 3.7 or 3.75 micrometers are removed, and wavelengths above 5.0 micrometers are removed.

In accordance with an embodiment of the present invention, the filtered image of the object 12, including the detected structural features, may be compared with a reference image. For example, a reference image may be generated from another object similar to the coated object that is known to be substantially free of defects. By comparing a substantially defect-free reference object to the coated object being inspected, manual or automated evaluations may be performed. The reference image used as the standard could be preprogrammed into a database and a comparison made between the reference image and the image created from paint under test. Acceptability criteria could be preprogrammed as well. For example, unacceptable areas could be highlighted in red and acceptable areas in green. Other colors could be selected, as well, such as gray for an area requiring more evaluation.

Figure 3:
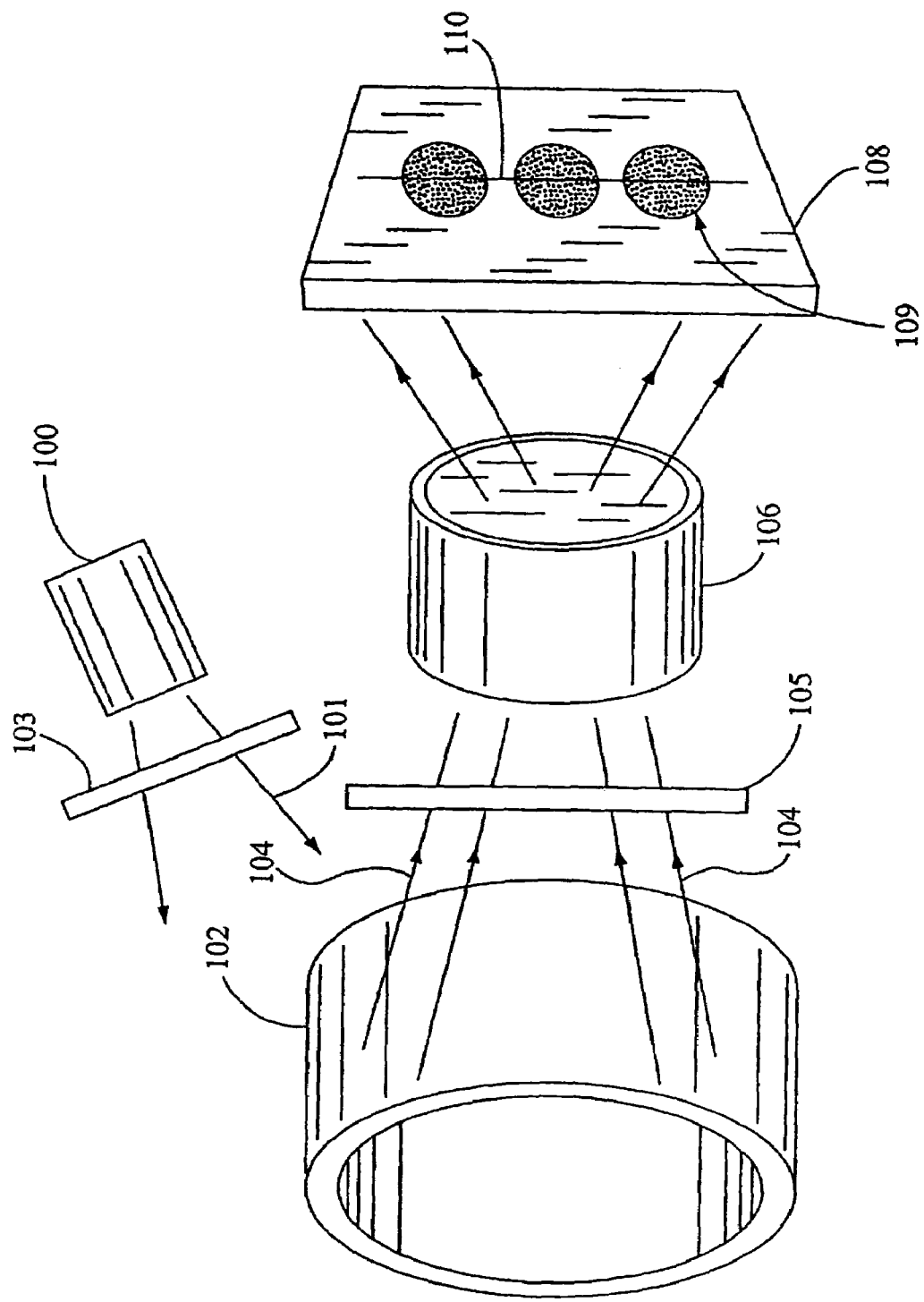
FIG. 3 is a schematic illustration of a system for detecting structural features of a coated object utilizing IR illumination of the object and a narrow bandwidth filter positioned between the object and a detector.
Figure 4:
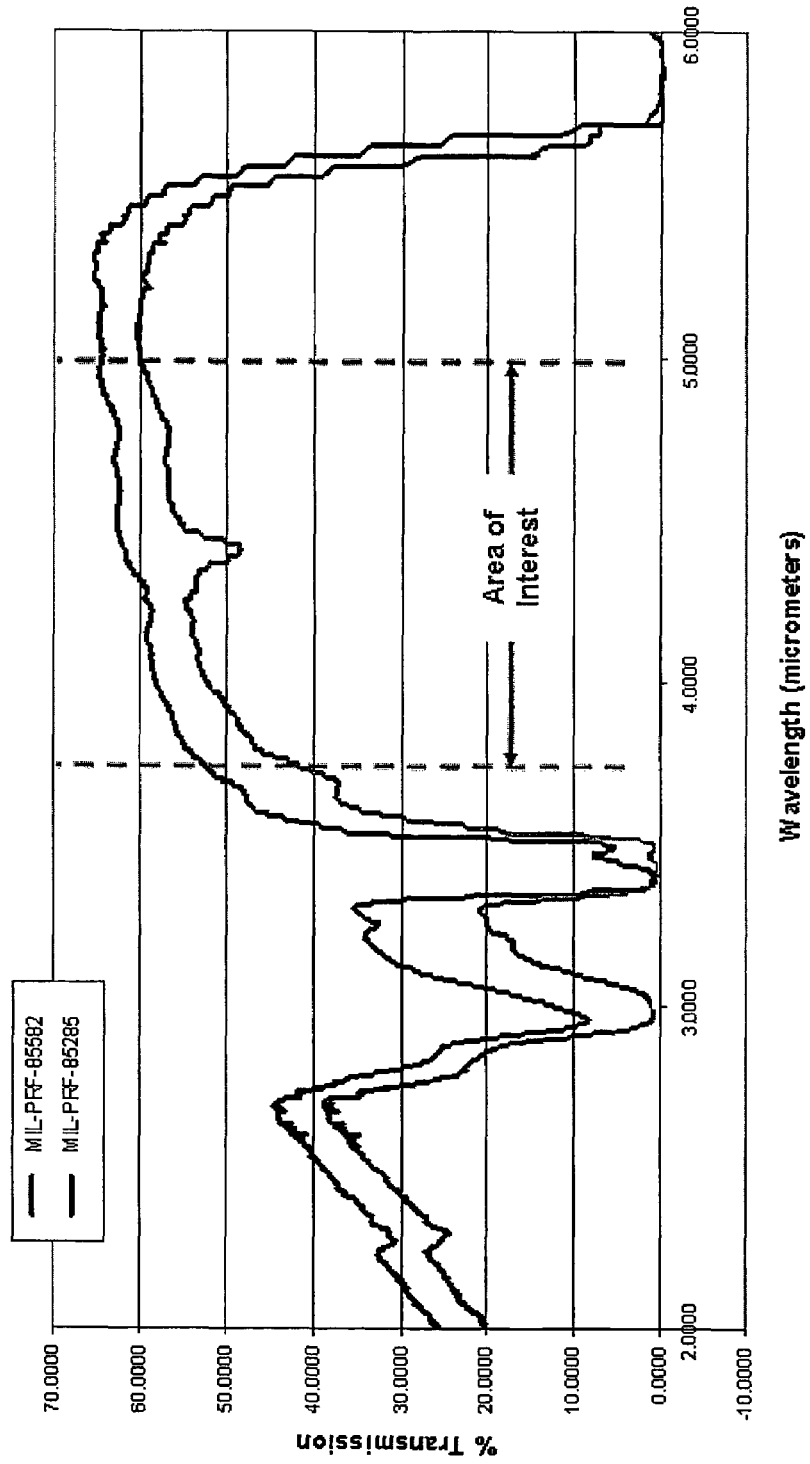
FIG. 4 depicts the FTIR spectra of an Aircraft Coating System. A strong absorbance peak occurs at 3.4 micrometers, which causes the IR to scatter and increases spectral noise. By using a narrow bandwidth filter (3.75-5.0 micrometer) in accordance with the present invention, a large percentage of scattering is eliminated.

FIG. 3 illustrates another system for detecting structural features of a coated object which utilizes IR illumination and a narrow bandwidth filter in accordance with an embodiment of the invention. An infrared light source 100 is used to cast infrared light 101 in the direction of a substrate 102 which is coated. Prior to reaching the substrate 102, the infrared light 101 may optionally pass through a first polarizer 103. The first polarizer 103 is operative to polarize the infrared light to a first selected polarity.

Light reflected by the substrate creates reflected light 104. The reflected light 104 passes through an optional second polarizer 105. The second polarizer 105 is operative to polarize the reflected light to a second selected polarity. For instance, the second polarizer 105 may be configured to polarize the reflected light 104 in a direction opposite to that of first selected direction, a method known as cross-polarity. In this case, light of the polarity modulated by the first polarizer 103 will not pass through the second polarizer 105. Polarizers may not be necessary in many instances because most coatings are not polarized in any certain orientation.

The portion of the reflected light 104 which was reflected off of regular areas of the substrate 102 will retain the polarity modulated by the first polarizer 103 and therefore will not pass through the second polarizer 105. However, the portion of the reflected light 104 which was reflected off of irregular areas, such as corrosion or rust, will have an altered polarity and will therefore pass through the second polarizer 105. Additionally, this optional polarization technique can reduce scattering by pigments in the coating which results in a clearer image of the substrate. Thus, only the portion of the reflected light 104 which was reflected off of irregular areas of the substrate 102 will pass through the second polarizer 105. The first polarizer 103 and second polarizer 105 may therefore operate in tandem to highlight the areas of the substrate 102 which are irregular because they are corroded or otherwise damaged. Additionally, the polarity modulated by the first polarizer 103 may be configured to allow viewing of the substrate 102 at various levels. This is because light of a polarity parallel to the substrate 102 will more easily reflect off of the coating, while light of a polarity perpendicular to the substrate 102 will more easily penetrate through the coating to the substrate beneath. Accordingly, it is possible to focus on either the surface of the substrate itself or on the surface of the coating. This methodology may be combined with the cross-polarity method described above in order to enhance particular features of the substrate at a particular level. It should be noted that although the first polarizer 103 and second polarizer 105 may be used in the fashion described and are therefore present in a potentially preferred embodiment, they are not necessary to the function of the present invention, and need not be included.

In accordance with the present invention, the reflected light 104 passes through a narrow bandwidth optical filter 106 similar to the narrow bandwidth filter 15 previously described. Coatings used on, for instance, aircraft components and assemblies are generally designed to be opaque in the visible range of light. Often, they are more transparent in the infrared range of light. Accordingly, certain wavelengths of light are more likely to pass through the coating to be reflected by the substrate beneath. The image created by the portion of the reflected light 104 having these wavelengths will represent an image primarily of the substrate 102 instead of the coating on the substrate. It is therefore desirable to focus on these wavelengths to the exclusion of others, and they become the selected wavelengths passed by the narrow bandwidth optical filter 106. The filter 106 need not be a single filter, but could be a series of filters, in order to tailor the bandpass wavelength to a specific wavelength range.

Subsequent to passing through the filter 106, the reflected light 104 reaches a detector in the form of a focal plane 108. A focal plane array (not shown) is positioned at a focal plane 108 for the purpose of receiving an image by the reflected light 104 at the focal plane 108. Structural features of the substrate 102, such as cracks 110 and corrosion are visible in this image 109. The focal plane array is operative to take this image generate it as a photograph, image on an LCD display, or otherwise represent it on a human-viewable medium.

The following examples are intended to illustrate the various aspects of the present invention and are not intended to limit the scope of the invention.

EXAMPLE 1

An aluminum panel coated with Military Grade Epoxy Primer, MIL-P-23377TY1 and Military Grade Polyurethane Top Coat, MIL-PRF-85285 TYI having a total thickness of approximately 2.1 to 3.3 mils (0.0021 to 0.0033 thousands of an inch) was imaged with a standard mid-wave Merlin™ IR Camera with the standard of detection limits of the focal plane in the mid-wave. The panel was illuminated with IR radiation. A filter comprising multiple filters having an adjustable bandwidth was used to produce images at settings of 3-5 micrometers, 3.5-5 micrometers, and 3.75-5 micrometers. During the imaging process, the panel was held at room temperature or approximately 70 to 75° F. FIG. 5 shows the results with the 3-5 micrometer filter; FIG. 6 shows the results with the 3.5-5 micrometer filter; and FIG. 7 shows the results with the 3.75-5 micrometer filter. The figures show the improved effect of glare removal. FIG. 5 shows the baseline image produced by the standard mid-wave Merlin™ IR Camera. This image has significantly increased brightness compared to the other images. The brightness is due in part to the reflection off the coating surface. This reflection is cut back by the moving the filter window from 3.0 to 3.5 microns, as shown in FIG. 6. Additionally moving the filter window up to 3.75 microns significantly enhances the window, as more glare is removed. The filter windows should be optimized not only for the camera and focal plane, but also for the IR transmission window of the coating. This process may be repeated until the IR energy reduction from the glare does not warrant any more glare removal from the image of the camera.

EXAMPLE 2

Figure 9:
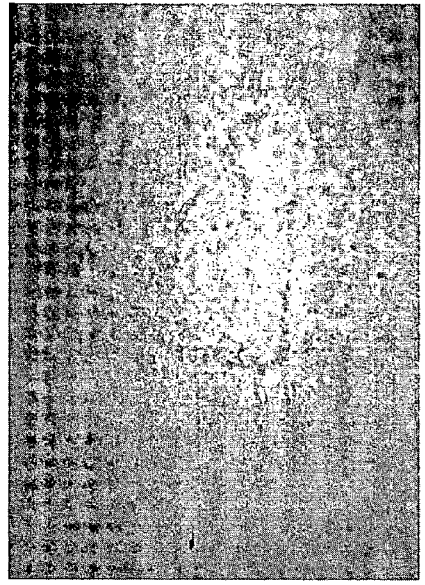
FIGS. 8-10 are photographic images of a coated substrate, illustrating unexpectedly improved detection of substrate damage under the coating with a system including a narrow bandwidth filter of the present invention (FIG. 10) in comparison with systems having broader bandwidth filters (FIGS. 8 and 9).
Figure 8:
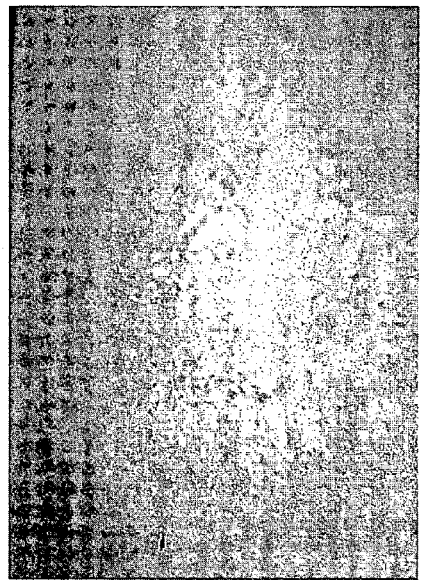
Figure 10:
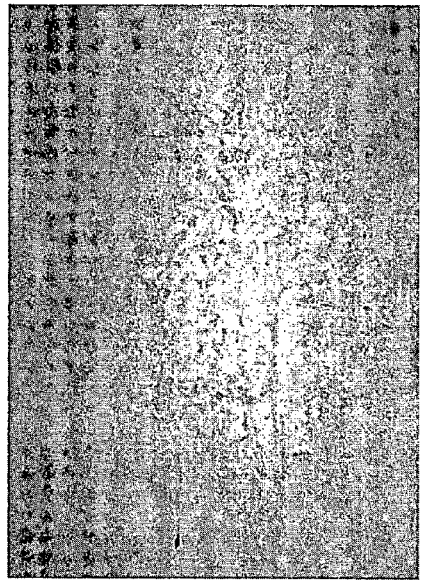

Example 1 was repeated, except the aluminum panel was coated with two coats of Military Grade Epoxy Primer, MIL-PRF-23377TYI and two coats of Military Grade Polyurethane Top Coat, MIL-PRF-85285TYI having a total approximate thickness of 4.2 to 6.6 mils (0.0046 to 0.0066 thousands of an inch). FIG. 8 shows the results with the 3-5 micrometer filter; FIG. 9 shows the results with the 3.5-5 micrometer filter; and FIG. 10 shows the significantly improved results with the 3.75-5 micrometer filter.

FIGS. 5-10 illustrate the improved contrast that can be seen after the incorporation of the narrow bandwidth filter of the present invention. In addition to self-illumination and IR-illumination techniques, the present narrow bandwidth filter is also applicable to active thermography to improve contrast and fidelity of images produced from the flash lamp process. The images produced by active thermography can also be of the reflectance mode or images produced from the thermographic cooling mode, as a function of time.

Whereas particular embodiments of this invention have been described above for purposes of illustration, it will be evident to those skilled in the art that numerous variations of the details of the present invention may be made without departing from the invention as defined in the appended claims.

The invention claimed is:

1. A system for imaging the surface of a substrate through a coating on the substrate, comprising:
    a detector positioned to receive infrared radiation from the substrate surface through the coating on the substrate; and
    at least one narrow bandwidth spectral optical filter between the substrate and the detector to pass infrared wavelengths from 3.75 to 5.0 micrometers to the detector, wherein the coating is substantially transparent to the infrared wavelengths passed from the substrate to the detector.

2. The system of claim 1, wherein the infrared radiation from the substrate comprises blackbody radiation from the substrate.

3. The system of claim 1, wherein the infrared radiation from the substrate comprises reflected infrared radiation from the substrate.

4. The system of claim 1, further comprising a source of infrared radiation illuminating the substrate.

5. The system of claim 1, wherein the detector comprises an infrared camera.

6. The system of claim 5, wherein the infrared camera detects mid-infrared radiation having wavelengths between about 3 and about 5 microns.

7. The system of claim 1, wherein the surface of the substrate comprises defects.

8. The system of claim 1, wherein the substrate comprises an aircraft component.

9. The system of claim 1, wherein the coating has a thickness of 0.5 to 12 mils.

10. The system of claim 1, wherein the coating comprises paint, a composite matrix material, primer, top coat and/or intermediate coatings.

11. The system of claim 1, further comprising means for displaying an image of the object including the detected structural features.

12. The system of claim 1, further comprising means for comparing an image of the object including the detected structural features with a reference image.

13. The system of claim 12, wherein the reference image is generated from another object similar to the coated object that is substantially free of defects.

14. The system of claim 1, further comprising means for comparing an image of the object where the filter may be selected to maximize signal-to-noise ratio and contrast between reflective surfaces through a coating.

15. A method for imaging the surface of a substrate through a coating on the substrate, comprising:
    generating infrared light from the substrate through the coating on the substrate;

filtering the infrared light with a narrow bandwidth filter which passes wavelengths within a range of from 3.75 to 5.0 micrometers; and receiving the filtered infrared light on a detector, wherein the coating is substantially transparent at the wavelengths passed from the substrate to the detector.

16. The method of claim 15, wherein the infrared radiation from the substrate comprises blackbody radiation from the substrate.

17. The method of claim 15, wherein the infrared radiation from the substrate comprises reflected infrared radiation from the substrate.

18. The method of claim 15, further comprising illuminating the substrate with infrared radiation.

19. The method of claim 15, wherein the coating has a thickness not to exceed 12 mils.

20. The method of claim 15, further comprising generating at least one image from the detector so as to visually reveal structural features of the substrate.

* * * * *

UNITED STATES PATENT AND TRADEMARK OFFICE
CERTIFICATE OF CORRECTION

PATENT NO. : 7,462,809 B2
APPLICATION NO. : 11/506701
DATED : December 9, 2008
INVENTOR(S) : Donald DiMarzio et al.

It is certified that error appears in the above-identified patent and that said Letters Patent is hereby corrected as shown below:

Column 4, Line 13
"BMS 10-172" should read -- BMS 10-72 --

Column 7, Line 15 should read
-- A focal plane array (not shown) is positioned at a focal plane 108 for the purpose of receiving an image 109 created by the reflected light 104 at the focal plane 108. --

Column 7, Line 19 should read
-- The focal plane array is operative to take this image 109 and generate it as a photograph, image on an LCD display, or otherwise represent it on a human-viewable medium. --

Signed and Sealed this

Eleventh Day of August, 2009

David J. Kappos
*Director of the United States Patent and Trademark Office*